US006561648B2

(12) United States Patent
Thomas (10) Patent No.: US 6,561,648 B2
(45) Date of Patent: May 13, 2003

(54) SYSTEM AND METHOD FOR RECONSTRUCTION OF ABERRATED WAVEFRONTS (75) Inventor: David Thomas, Bartlett, TN (US)

(73) Assignee: David E. Thomas, Bartlett, TN (US)

( * ) Notice: Subject to any disclaimer, the term of this patent is extended or adjusted under 35 U.S.C. 154(b) by 0 days.

(21) Appl. No.: 09/863,914

(22) Filed: May 23, 2001

(65) Prior Publication Data

US 2003/0028115 A1 Feb. 6, 2003

(51) Int. Cl.[7] ................................................. A61B 3/10
(52) U.S. Cl. ....................................................... 351/221
(58) Field of Search ................................ 351/200, 205, 351/206, 207, 208, 211, 213, 216, 219, 220, 221, 246, 247; 356/388, 391, 398; 600/300

(56) References Cited

U.S. PATENT DOCUMENTS

| 3,923,400 | A |   | 12/1975 | Hardy ........................ 356/107 |
| 4,943,709 | A |   | 7/1990  | Grinberg et al. ......... 250/201.9 |
| 5,042,939 | A | * | 8/1991  | Zayek ........................ 351/205 |
| 5,108,174 | A |   | 4/1992  | Lippens ...................... 356/124 |
| 5,120,128 | A |   | 6/1992  | Ulich et al. ................. 356/121 |
| 5,229,889 | A |   | 7/1993  | Kittell ........................ 359/849 |
| 5,537,162 | A |   | 7/1996  | Hellmuth et al. .......... 351/206 |
| 5,684,545 | A |   | 11/1997 | Dou et al. ..................... 349/1 |
| 5,787,890 | A |   | 8/1998  | Reiter et al. ................ 128/665 |
| 5,825,476 | A |   | 10/1998 | Abitol et al. ............... 356/124 |
| 5,828,455 | A |   | 10/1998 | Smith et al. ................ 356/354 |
| 5,892,569 | A | * | 4/1999  | Van de Velde .............. 351/221 |
| 5,943,117 | A |   | 8/1999  | Van de Velde .............. 351/221 |
| 5,978,053 | A |   | 11/1999 | Giles et al. .................... 349/17 |
| 6,000,799 | A |   | 12/1999 | Van de Velde .............. 351/205 |
| 6,059,773 | A |   | 5/2000  | Maloney et al. ................ 606/4 |
| 6,070,981 | A |   | 6/2000  | Mihashi et al. ............. 351/212 |
| 6,086,204 | A |   | 7/2000  | Magnante ................... 351/212 |
| 6,089,711 | A |   | 7/2000  | Blankenbecler et al. .... 351/160 |
| 6,112,114 | A |   | 8/2000  | Dreher ........................ 600/476 |
| 6,379,005 | B1| * | 4/2002  | Williams et al. ............ 351/211 |

OTHER PUBLICATIONS

David Thomas, "Digital Image Reconstruction Using the Technique of Parallel Laser Ray Tracing(PLRT)" Apr. 18, 2001.
Tracey Technologies, http://www.tracytech.com/products.htm.

* cited by examiner

Primary Examiner—Marvin M. Lateef
Assistant Examiner—John R. Sanders
(74) Attorney, Agent, or Firm—Haynes & Boone, LLP (57) ABSTRACT A method and apparatus for improving the resolution of fundus images and correction of optical aberrations is described in which a bundle of electromagnetic beams is directed into an optical system and the reflected electromagnetic beams are recorded by a sensor. A processor may control the energy source to provide a plurality of different electromagnetic bundles to image the entire optical system. The reflected electromagnetic beams recorded by the sensor are compared to the original electromagnetic bundle configurations to calculate the aberrations of the optical system of interest. Among other applications, the calculated aberrations may be used to construct accurate fundus images, provide input for laser surgery of the eye, fabricate corrective lenses and provide accurate digital images of structures sensed through imperfect optical systems.

34 Claims, 7 Drawing Sheets

SYSTEM AND METHOD FOR RECONSTRUCTION OF ABERRATED WAVEFRONTS

FIELD OF THE INVENTION

The present invention may have applications in all optical fields were it is desired to reconstruct or correct aberrated wavefronts. A specific embodiment of the present invention may be particularly adapted to reconstruct accurate fundus images, provide input for laser surgery of the eye, fabricate corrective lenses and provide accurate digital images of structures sensed through imperfect optical systems.

BACKGROUND OF THE INVENTION

Aberrations of optical signals occur in many systems and applications. For example, recent interest has been focused on identifying aberrations in the optics of the human eye and correcting these aberrations where possible. Identification of the aberration structure in the optical system offers the possibility of imaging surfaces beyond the aberrating structure or correcting the wavefront exiting the aberrating structure by reshaping the structure or the incident wavefront. In a report entitled "Objective Measurement of Wave Aberrations of the Human Eye With the Use of a Hartmann-Shack Wave-Front Sensor", Liang et al., J. Opt. Soc. Am. A., volume 11, number 7, pp. 1–9, July 1994, the authors disclose the use of a Hartmann-Shack wavefront sensor to measure the wave aberrations of the human eye by sensing the wavefront emerging from the eye produced by the retinal reflection of a focused light beam on the fovea. Due to the limitations of the disclosed system, attempts to improve the system have been made and are disclosed in U.S. Pat. No. 6,095,651 to Williams et al.

Figure 1:
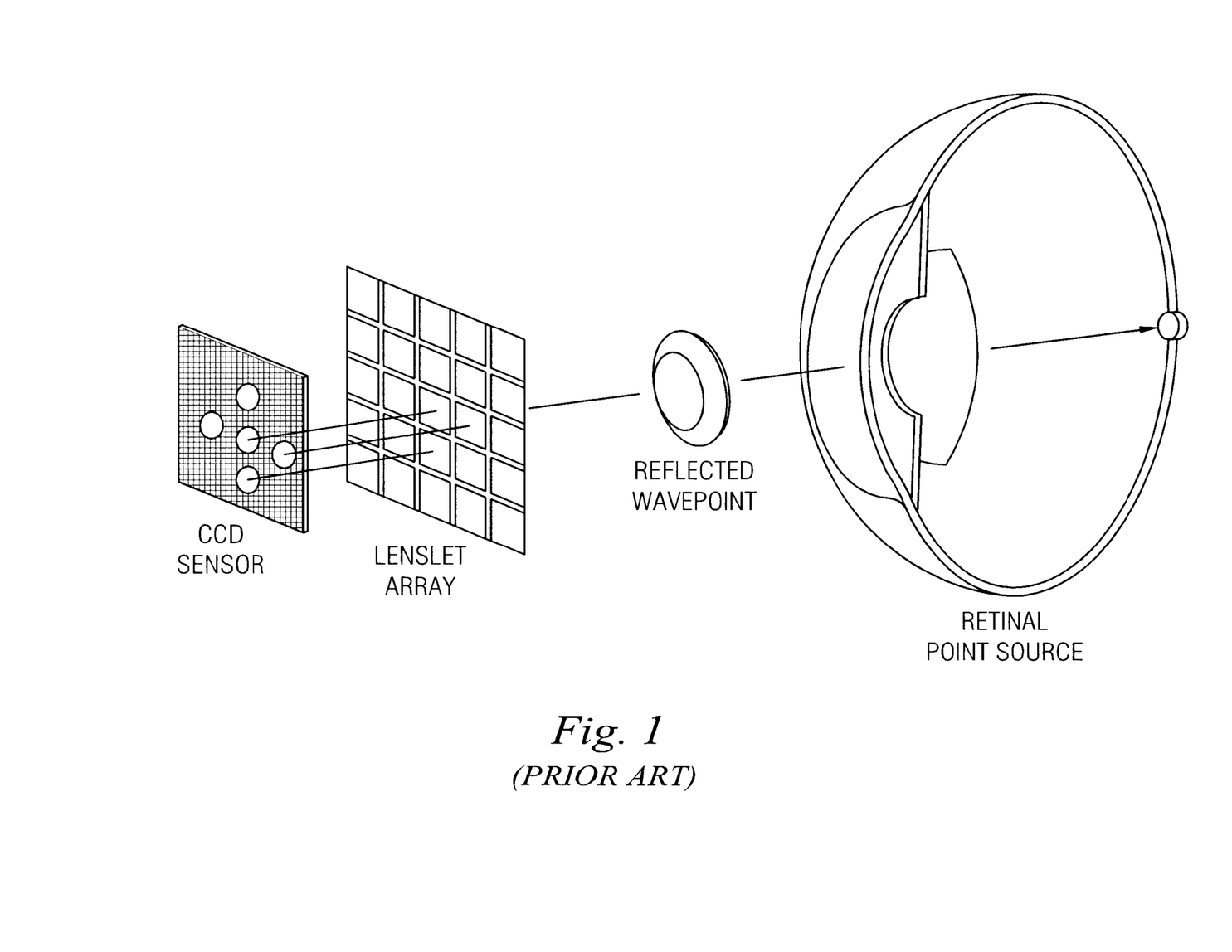
FIG. 1 is a perspective view of a prior art sensing device.
Figure 2:
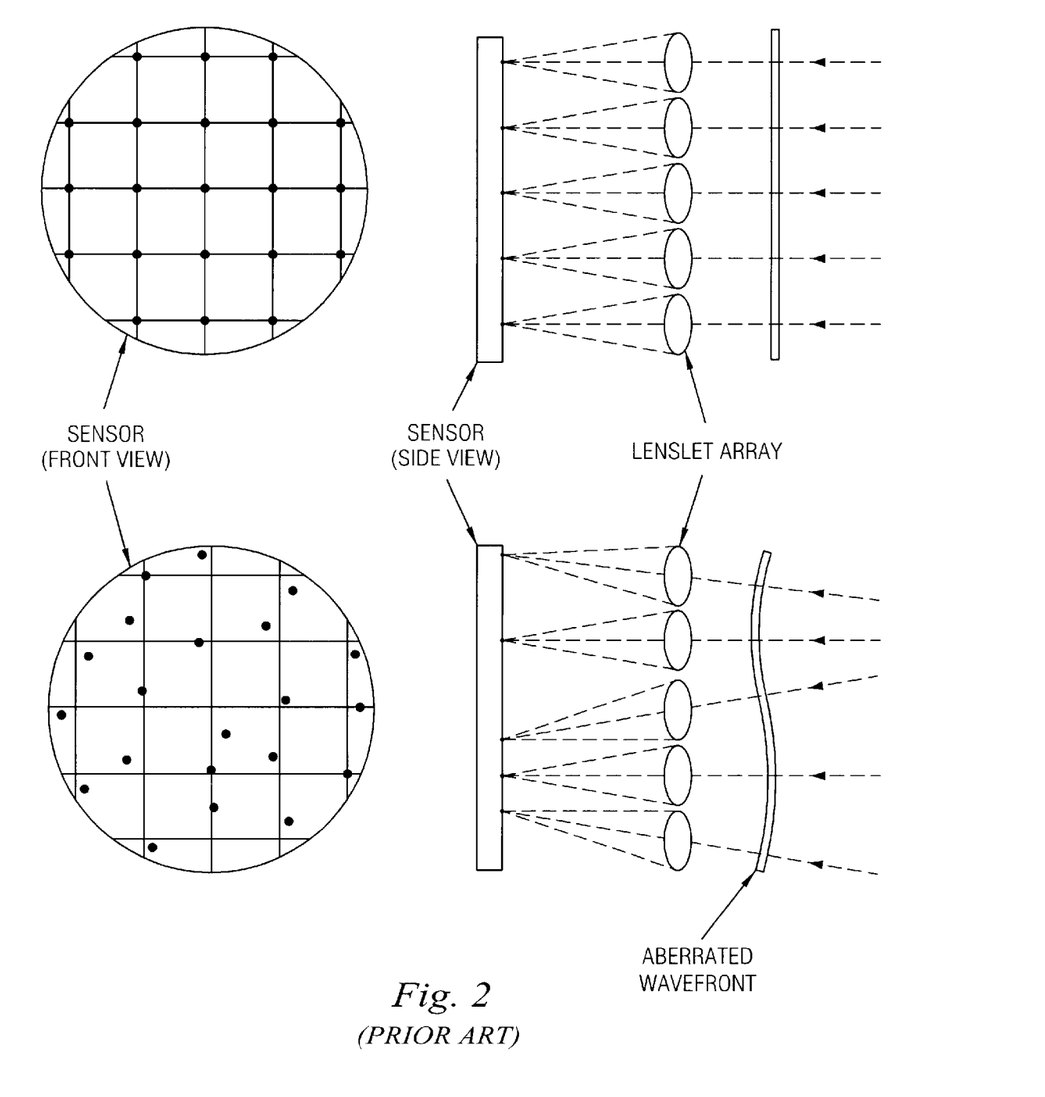
FIG. 2 is an illustration of a lenslet array according to FIG. 1 and wavefronts incident thereon.

The basic diagram of a Hartmann-Shack system is shown in FIGS. 1 and 2. FIG. 1 shows a schematic drawing of a beam of light reflected off the retina (incident beam and beam-shaping optics not shown). In general terms, a ray of light is projected into the eye and reflected off the retina. The reflected wavefront is monitored and spot locations are recorded by a CCD camera or other imaging device. Aberrations are quantified by the deviation of these select rays from the ideal location of rays in an aberration-free system (see FIGS. 2a and 2b).

The device presented in U.S. Pat. No. 6,095,651 projects a single (relatively large diameter) laser beam into the eye. The incident beam covers the entire pupil area (6 to 8 mm in diameter). Before entering the eye, the laser source output is collimated to form a single beam with a parallel shape. The single beam enters the eye where the human optics focus the beam on the retina. The beam is reflected from the retina and passes back through the eye. For this reason, the technique is sometimes referred to as a "double pass" method—light passes through the optics of the eye twice. The emerging beam travels through multiple lenses (imaging optics) until it finally strikes the HS lenslet array (FIG. 1). The HS lenslet array separates the beam into smaller beamlets, which are focused into spots on an imaging device (typically a CCD camera). The location or displacement of the spots is recorded by the CCD camera.

FIG. 2 illustrates an example of how a uniform wavefront is sensed by the CCD camera and how an aberrating medium changes the wavefront sensed by the CCD camera. The wavefront carries a description of how the original (incident) beam was affected by the optics of the eye. The displacement of the spots from the ideal location roughly corresponds to the aberration properties of the wavefront of the emerging laser beam. If the wavefront is not aberrated or distorted at the location of a particular HS lenslet, the corresponding spot will not be displaced. If the wavefront is highly aberrated then the corresponding spot will be displaced more. The difference between the ideal location and displaced location is the general angle or slope of the wavefront at the lenslet location. Unfortunately, aberrations in the individual lenslets may also contribute to the difference between the ideal location and the displaced location. The slope of the wavefront at many different locations allows one to fit the data to a model of the wavefront.

Previous researchers have applied the re-constructed wavefront information to a compensating device like a deformable mirror. The deformable mirror allows control of a second beam of light (e.g. a flash) so that it is corrected for the aberrating properties in the eye. This technique has demonstrated improved imaging of the retina but fails to provide precise data necessary for accurate imaging.

More recently, as described in "Laser Ray Tracing Versus Hartmann-Shack Sensor for Measuring Optical Aberrations in the Human Eye", Moreno-Barriuso et al., J. Opt. Soc. Am. A., Vol. 17, No. 6, pp. 974–985, have described a technique for using small laser beams they called "pencils of light" to measure aberrations in the eye. They termed the technique "Laser Ray Tracing." In the work, they used a scanning mirror to create a single, small diameter, beamlet that could be moved around the eye in sequential fashion. According to the authors, the technique consists of delivering, sequentially, a series of light pencils (nonexpanded laser beams) coming from the same point object but passing through different locations at the exit pupil plane. The trajectory of the light pencils (rays) is controlled by means of a two dimensional XY optical scanner driven by moving magnet actuators and by additional optics (collimator) when needed. Using this system, the authors were only able to process 4–5 rays per second.

Therefore, there remains a need for improved systems and method of compensating for aberrated wavefronts.

SUMMARY OF THE INVENTION

In one aspect of the present invention, a system is provided for imaging through an imperfect optical system. Preferably, the system comprises an energy source generating a plurality of electromagnetic beams having a first configuration for simultaneous transmission through the optical system. A sensor is provided for detecting the plurality of electromagnetic beams after passing through the optical system. A processor is provided that is adapted to utilize the sensed information to calculate the approximate aberrations in the optical system.

In a further aspect of the present invention, an apparatus is provided for use in performing surgery on a living eye. The apparatus may comprise an energy source generating a plurality of electromagnetic beams for simultaneous transmission into a living eye. A camera or other suitable sensor may be located adjacent the eye and in the optical path of a substantial number of the plurality of electromagnetic beams reflected from the living eye to produce digital outputs corresponding to the sensed location of the plurality of electromagnetic beams. A processor receives outputs from the camera or sensor and converts the output signals to a digital signal representative of the optics of the living eye. In a preferred aspect of the invention, surgical equipment may utilize the representative digital signal for performing surgery on the living eye. Still further, the representative digital signal may be used to generate a corrective optic device that corrects all or a part of the sensed aberrations.

In yet a further aspect of the present invention, an apparatus is provided for generating high resolution fundus images of the living eye. Preferably, the apparatus comprises an energy source adapted to generate a plurality of electromagnetic beams in at least one configuration for simultaneous transmission into the living eye. A sensor is included to receive a reflected image of a substantial number of said electromagnetic beams from the living eye and generate a corresponding output signal. A processor may use the output signal to determine wave aberrations of the living eye based on the difference between the first configuration transmitted into the living eye and the reflected image. In a more preferred aspect, a camera receives a fundus image of the living eye and a processor corrects the fundus image based on the calculated wave aberrations. The corrected fundus image may be displayed on a monitor. In still a more preferred aspect, a processing element controls the energy source to generate a plurality of different configurations of the electromagnetic beams.

The present invention also contemplates a method for detecting aberrations of the living eye. The method comprises initially generating a plurality of electromagnetic beams in a first configuration and transmitting the first configuration of electromagnetic beams into a living eye. The electromagnetic beams reflect off structures in the eye and may be received and converted to corresponding digital signals. The digital signals may be used for calculating wave aberrations of the eye. In a preferred aspect, an energy source may be controlled to generate a plurality of electromagnetic beam configurations to accurately detect aberrations of the living eye. Still more preferably, a reference sensor can be used to receive the electromagnetic beam configuration prior to transmitting to the eye. This may be used to improve the accuracy and efficiency of mathematical calculations. In a further alternative, the reference sensor may be used in conjunction with the primary sensor to control an illumination source to generate a beam with an aberrated wavefront corresponding to sensed aberrations in the living eye.

Related objects and advantages of the present invention will be apparent from the following description.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The system and method according to the preferred embodiments of the present invention employ a spatial light modulator (SLM), diode laser array, or similar device to create many thousands of tiny rays, or beamlets, of laser energy that trace a path through the distorting media of an optical system, particularly an eye. Each ray traces a path through a slightly different region of the eye than its neighbor. As the ray passes through the eye, it is distorted by the media in the optical path. A sensor, such as a CCD camera, records the location of each beamlet after it has traced a path through the eye. In a preferred embodiment, a second, reference sensor, can be used to provide information about the ideal location for each beamlet—not having traveled through the distorting media. A computer system records the locations of the ideal and distorted rays and generates a pixel map.

This process can be performed simultaneously for many thousands of rays traveling through different regions of the eye to generate a pixel map. A subsequent image is acquired and reconstructed using information in the pixel map. In a preferred aspect, the image may be reconstructed in an entirely digital manner since it is possible for the resolution of the pixel map to approach the resolution of the acquired image. Further, information from the pixel map may be used to provide information about the structures of the eye such that surgery or other correction may be performed to improve a patient's vision. Thus, the present system and method permit one to measure the optical properties of the eye in much more detail and more quickly than with previous techniques. One trained in the art will quickly realize the importance of the tremendous increase in resolution.

Figure 5:
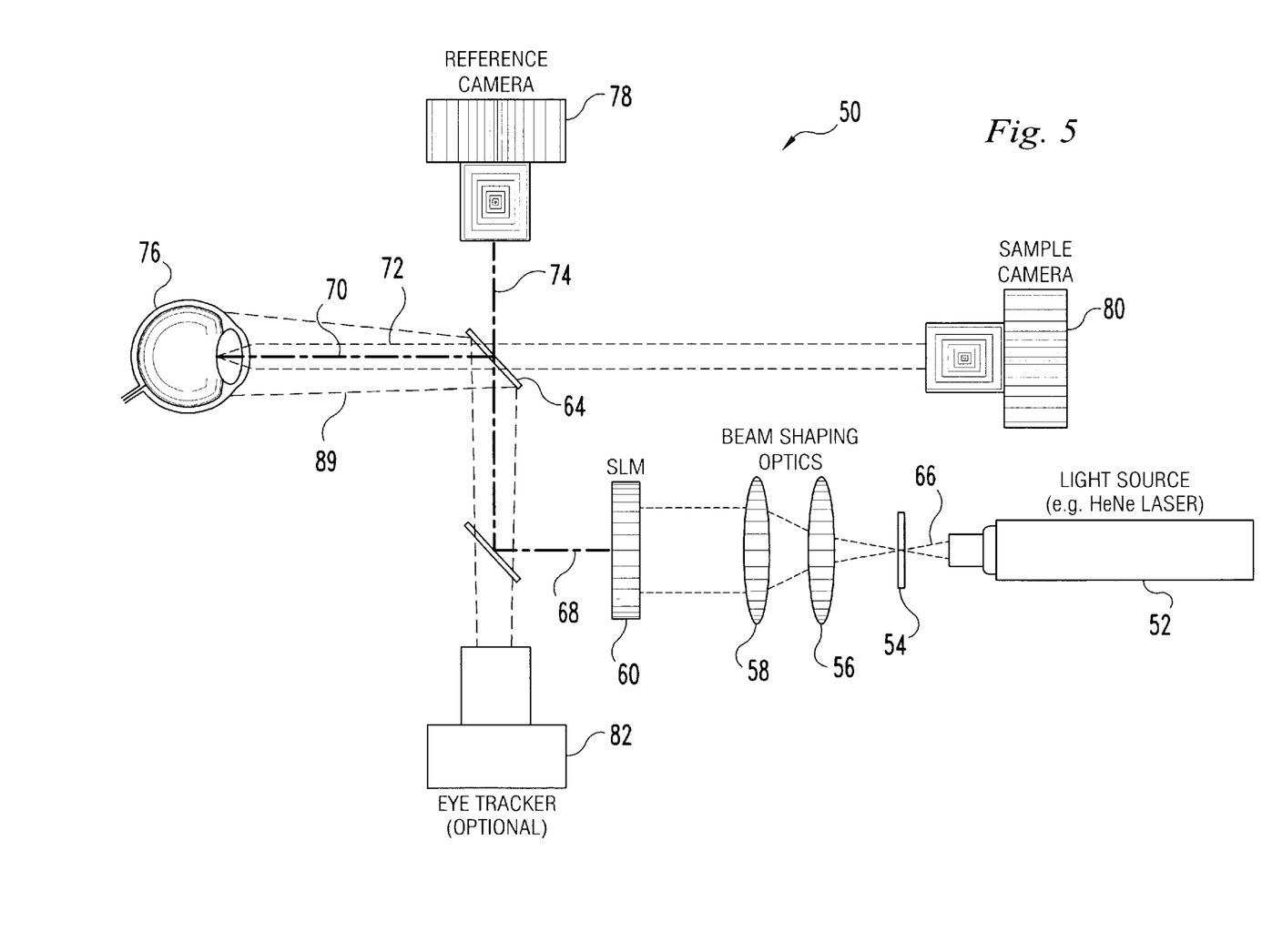
FIG. 5 is a diagrammatic view of one embodiment of the present invention.

A schematic drawing of a system 50 constructed in accordance with a preferred aspect of the present invention is shown in FIG. 5. In system 50, an energy source 52 generates a beam 66 of electromagnetic energy. Preferably, energy source 52 is a HeNe laser generating a beam of visible light. As shown in FIG. 5, beam 66 initially passes through spatial filter 54 and is expanded by lens 56. Beam 66 passes through a second lens 58 that collimates the beam. While the above described beam-shaping optics are disclosed for the purpose of illustration, other known techniques for the generation of a beam usable with the present invention are also contemplated.

In a preferred aspect of the present invention, beam 66 is directed at spatial light modulator (SLM) 60 which separates beam 66 into a bundle of many smaller beamlets forming ray bundle 68. It is contemplated that SLM 60 may be a transmissive or reflective SLM. Preferably, ray bundle 68 comprises a plurality of parallel beams of light. While it is possible to utilize converging, diverging or overlapping beams of light, as explained further herein, the task of indexing each beam would be further complicated by such an approach. It is contemplated that as the incident beam of electromagnetic energy is divided into many smaller beamlets certain aberrations may be induced into the beamlets. Those skilled in the art will recognize that one may utilize additional optics to improve the beamlet quality before transmission to the eye. However, as explained more fully herein, the beamlets may be sampled prior to transmission to the eye and detected aberrations in the beamlets considered by the system when calculating sensed aberrations in the optical system.

Ray bundle 68 passes through a beam splitter 64 that splits the bundle into two sets. A first ray bundle 70 enters an optical system, shown for the purposes of illustration as a human eye 76. The second ray bundle 74 is imaged onto the sensor of a reference camera 78. First ray bundle 70 that is incident on eye 76 passes through the lens structure of the eye, is reflected off the retina and passes back through the lens structure of the eye. These emerging beamlets 72 are imaged on the sensor of a sample camera 80. The location of each ray making up ray bundle 68, represented by a spot in the recorded image, is recorded by both sample camera 80 and reference camera 78.

Figure 3:
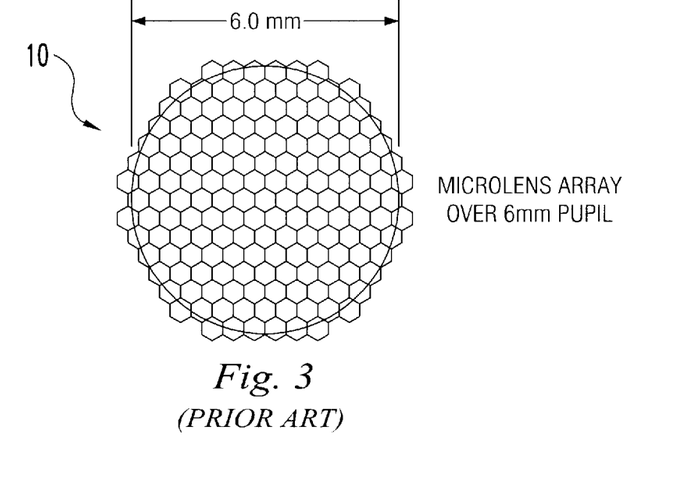
FIG. 3 is an illustration of a lenslet array according to FIG. 1 in relation to a human pupil.
Figure 4A:
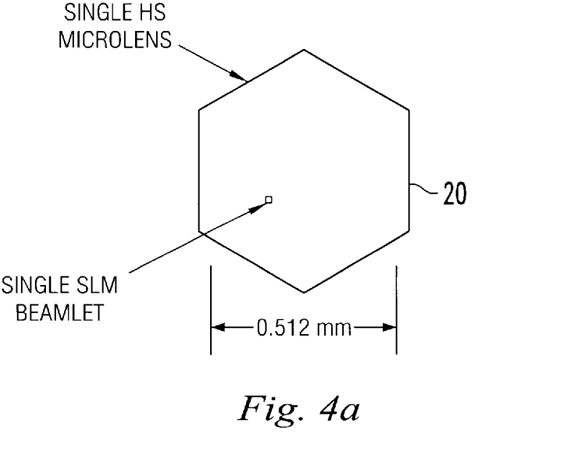
FIG. 4a is an illustration of a lenslet of the array of FIG. 3 in relation to a single beam in accordance with the present invention.
Figure 4B:
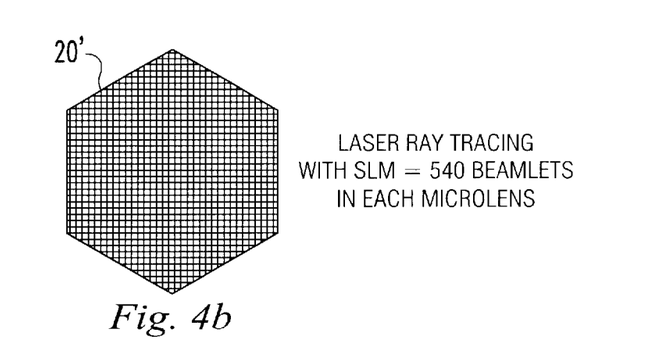
FIG. 4b is an illustration of the lenslet of FIG. 4a showing the scanning density possible in a preferred aspect of the present invention.

Prior devices have utilized an array of microlenses to digitize the reflected wavefront of a single beam of light. As shown in FIG. 3, the use of relatively large microlenses in array 10 provides only very rough definition of a reflected wavefront leaving the human eye. As shown in FIG. 4a, current microlens 20 has a width of 0.512 mm. Still referring to FIG. 4a, a single beamlet according to the present invention may have a width of 16 microns, substantially smaller than available microlens 20. As shown in FIG. 4b, the significant reduction in the width of the incident light beam permits approximately 540 beamlets to probe the same area previously probed with only one microlens 20'. Those skilled in the art will appreciate that the significant increase in probe beamlet density will have corresponding significant increases in wavefront aberration calculations and subsequent image reconstruction.

While it is contemplated that any device may be used to create the bundle of beamlets, there are three different preferred techniques for providing the beamlets. Each of the three techniques is able to modulate laser light so that very small beamlets could be turned on or off, providing a programmable array or bundle of light rays. These techniques may include by way of example, but without limitation on alternative approaches: (1) reflective SLM's based on CMOS technology utilizing micro-electromechanical systems to control at least partially reflective surfaces; (2) transmissive SLM's (e.g. liquid-crystal device); or (3) an array of vertical cavity surface emitting laser (VCSEL) diodes.

Figure 6:
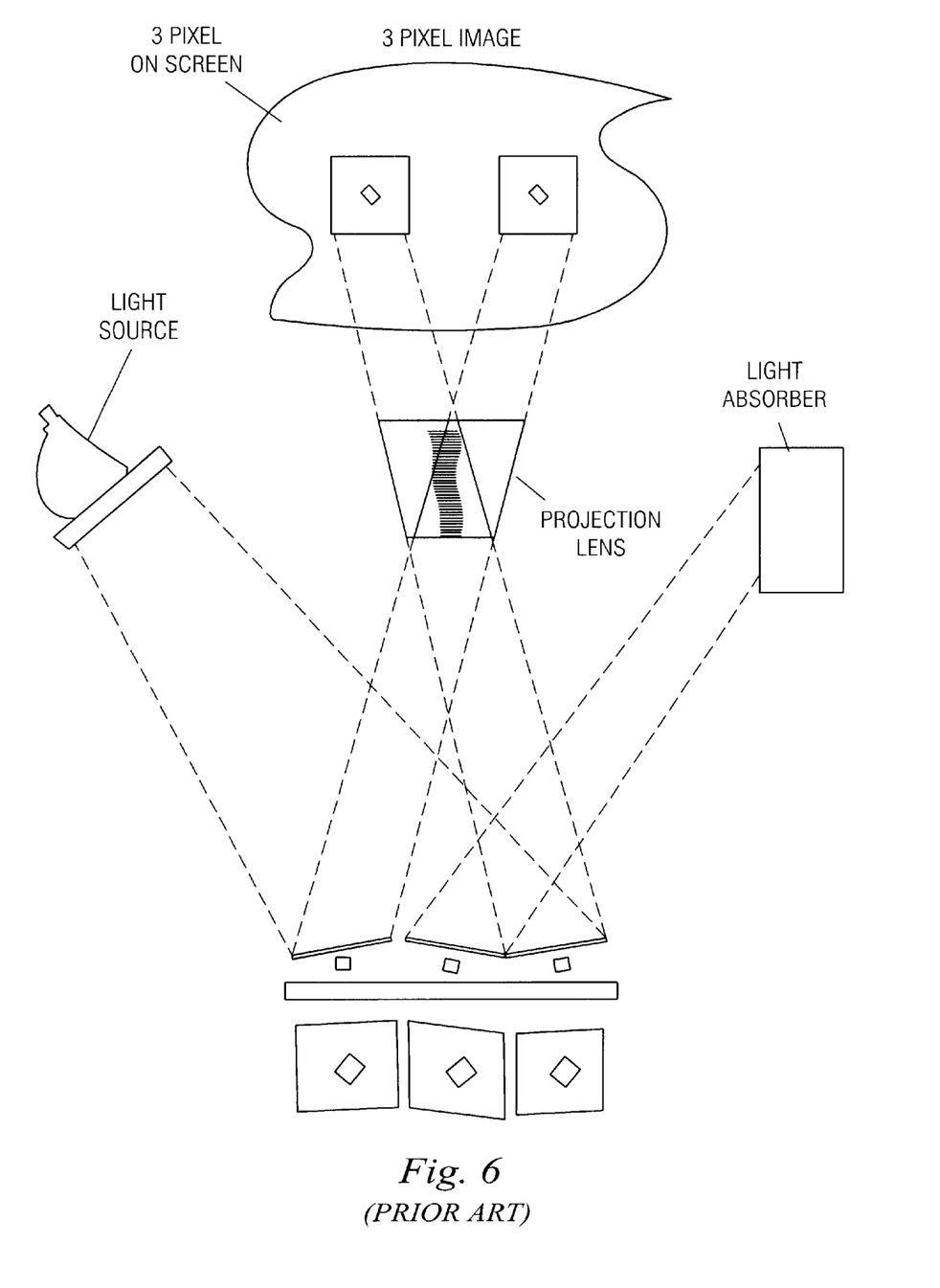
FIG. 6 is a partial diagrammatic view of a SLM component utilized with the present invention.

Referring to FIG. 6, a reflective SLM has been developed by Texas Instruments to address the emerging digital TV market. The TI Digital Micromirror Device (DMD) contains over 1 million individually addressable aluminum mirrors that can be rotated so that incident light is reflected into an imaging lens ("ON" state) or away from an imaging lens ("OFF" state) as shown in FIG. 6. Each individual micromirror is 16 microns square with a 1-micron gap between mirrors. In essence, this provides a mechanism for turning a 1-inch beam of light into approximately 1.3 million individual rays.

The schematic drawing of FIG. 6 shows a DMD micromirror configuration with incoming light hitting the three mirror pixels. The two outer mirrors are turned "on" to reflect the light through the projection lens and onto a target (e.g. a video screen). These two "on" mirrors produce square, white pixel images. The central mirror is tilted to the "off" position. This mirror reflects light away from the projection lens to a light absorber so no light reaches the screen at that particular pixel, producing a square, dark pixel image. In the same way, the remaining mirror pixels reflect light to the screen or away from it. Thus, it will be understood that a micromirror device similar to the DMD device may be utilized with the present invention to transmit small portions of a generated source beam to the optical system of interest. Individually addressable mirrors may be turned "on" or "off" to generate a ray bundle having features consistent with the present invention.

Liquid-crystal technology has been developed for computer and electronic displays. Recently, the technology has been used as a transmissive spatial light modulator in conjunction with HS wavefront sensors after the wavefront has already been measured. In the applications with the HS wavefront sensors, the device is used as an electronically controlled (adaptive) optical element in the system that can alter the eye's refractive state (similar to spectacle lenses). The information gathered by the HS device is used to program the liquid-crystal device to correct for aberrations in the eye. However, it will be understood by those skilled in the art, that the use of the transmissive spatial light modulator may be used in accordance with the present invention to split the probe beam prior to its entrance to the eye.

It is also possible to create a bundle of rays using Vertical Cavity Surface Emitting Laser (VCSEL) diodes. Very small diodes have been developed that emit a laser beam from their surface. These diodes can be manufactured so that an array is stacked closely together. Each diode could be turned on or off, creating the same affect as the SLM.

Each of the disclosed devices may be more generally referred to as programmable energy sources for generating various arrays of light beams. As will be appreciated, a plurality of small beams may be created with other known optical components (slotted fixtures, masks, etc.) without deviating from the scope of the present invention. However, in a preferred embodiment, programmable SLM devices are employed in combination with a laser source. The flexibility of a programmable SLM means that one can configure a bundle of rays to a first pattern, perform calculations, then repeat the steps using a bundle of rays with a different second pattern. It would be possible to sequentially re-create the wavefront using many different ray bundle patterns. In addition to spot location, other information can be obtained from the images. For example, the relative intensity of each spot can be used to identify areas of absorption indicating possible ocular pathology like cataracts. Different spot sizes can indicate regions in the eye that have high dispersion (scatter light).

For use in human eye evaluation, a fixation device can be used to assist the subject in fixating and focusing on a fixed point along the optical axis. Such a fixation device is shown in U.S. Pat. No. 5,989,194, which is incorporated by reference herein in its entirety. Preferably, the system may include a third camera (not shown) to assist in patient alignment and/or as an eye tracker. In eye-tracking mode, this camera may be used to monitor the position of the eye. A signal would be supplied to the SLM, which would turn beamlets on or off corresponding to the location of the eye. In other words, the desired beam pattern may be made to move so that it followed the eye. In a patient alignment mode, this camera may provide an image of the patient with respect to an alignment axis, assisting a technician with positioning the patient prior to a test.

In still a further feature of a preferred embodiment of the present invention, sensors within cameras 78 and 80 may include chromatic sensitivity. Therefore, if the wavelength of the incident beam can be separated as a function of location in the image, the color of the spot can be used to reduce computational complexity. Further, the reference camera also increases accuracy since aberrations or artifacts in the beam shaping optics may be subtracted from the sample image.

Figure 7A:
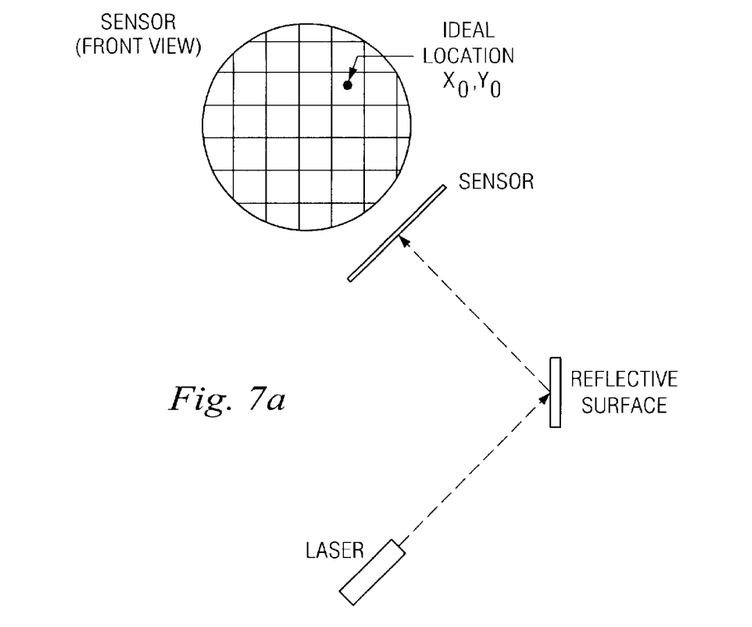
FIG. 7a is a diagrammatic view of a reflected electromagnetic beam sensed on an ideal path.
Figure 7B:
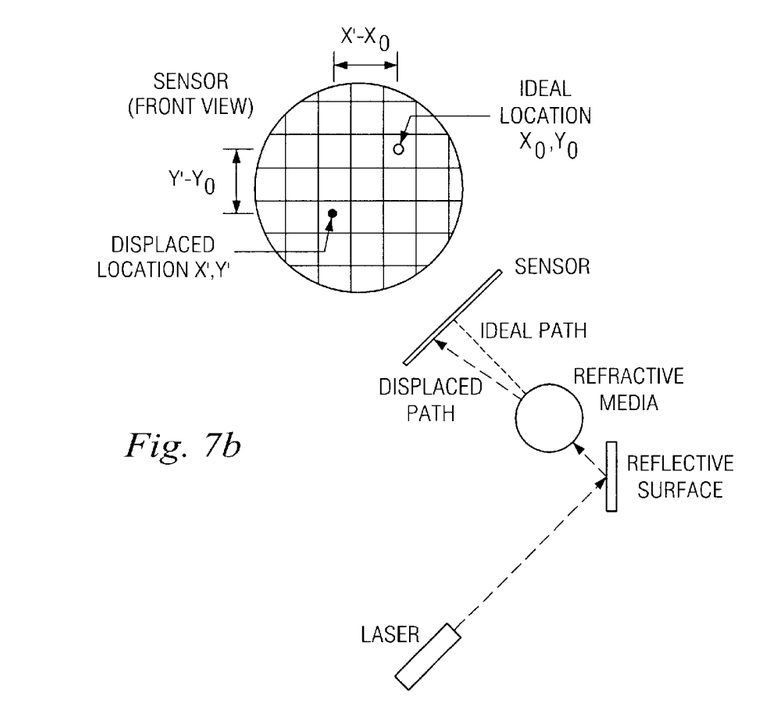
FIG. 7b is a diagrammatic view of a reflected electromagnetic beam sensed through a refractive media.

Referring now to FIGS. 7a and 7b, there is shown a schematic diagram of a single ray detected by a sensor. The centroid of each spot is identified by a computer (see FIGS. 8 and 9) for both the reference and sample images. For each ray, the difference between locations in the reference and sample images correlates to the amount of aberration in the wavefront. Note that aberrations due to imperfections in the components of the device may be accounted for, and subsequently eliminated, by calibration. This process of comparing the location of each ray in reference and sample images is repeated for all rays in the bundle. The wavefront is re-created using mathematics described later.

Correct calibration of any wavefront sensor is helpful to acquire accurate measurements. Previously, this has been difficult to accomplish—requiring the technician to move or replace lenses and/or targets to achieve the desired results. In the disclosed system, calibration may be accomplished with the aid of reference camera 78 positioned after the beam shaping optics as shown in FIG. 5. The reference camera may record the location and intensity of each beamlet prior to entrance into the optical system to be evaluated. This data may be used to subtract out any aberrations or artifacts caused by the illumination source or beam-shaping components, thereby increasing the accuracy of the measurements from the sample camera 80.

In a preferred approach, the system may be calibrated by using a sequence of steps. In at least one such sequence, the SLM is initially programmed so that a single beam is formed. This beam is projected onto the reference camera, as shown in FIG. 7a. The image of the single beam is recorded and the centroid of the spot is calculated by a computer (see FIGS. 8 and 9). The process of using a single beam or small group of beams is repeated at many different locations. A computer may then calculate the difference between the recorded spot locations and the ideal location. The ideal location is defined by the physical location of components in the SLM used to create the beams. The difference between the ideal location and the sensed location is typically due to aberration in the SLM or other beam shaping optics.

It is also preferred that the system is calibrated to compensate for misalignment in the optical system. Prior to making a wavefront measurement, the SLM may be programmed so that a single beam is formed. This beam is projected onto a reflective target positioned at the plane of the optical system to be analyzed. An image of the single beam is recorded by the reference camera and an image of the reflected single beam is recorded by the primary camera. This provides a point of origin for both cameras. It does not matter if that point is physically different for the two cameras. All subsequent measurements are made relative to the point of origin. The process may be repeated at several different locations to create a reference frame for each image. The system may be programmed to turn on many beamlets and record the spot locations with both cameras. The difference in spot location between reference and sample camera is the aberration in the system. Once the system has been calibrated, the sequence of measuring the wavefront may be commenced.

The reference camera provides the flexibility of compensating for imperfect alignment of the patient or optical components. Nothing in the system needs to be moved once the target optic system is in substantial alignment with the optical path of the system.

Figure 8:
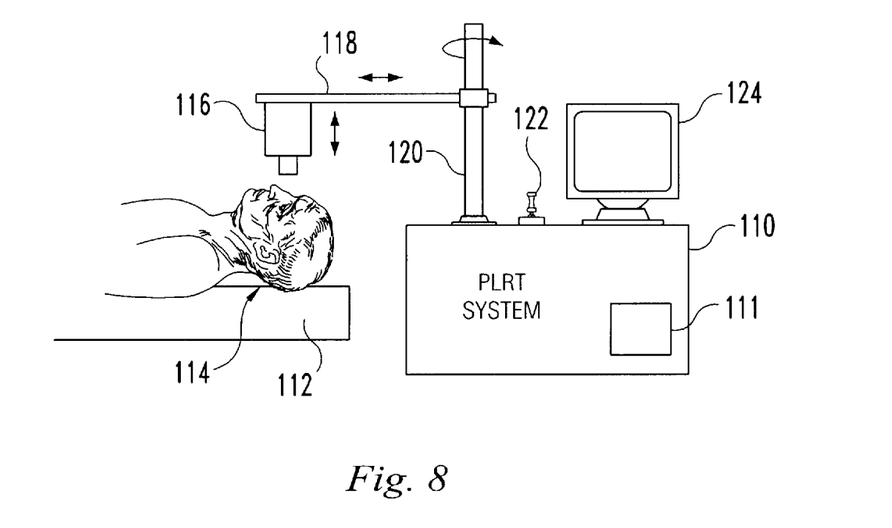
FIG. 8 is a diagrammatic view of a first system incorporating the present invention.

Referring now to FIG. 8, a microsurgery apparatus is disclosed in accordance with a preferred aspect of the invention. The microsurgery apparatus, which may be utilized for LASIK type procedures or other microsurgery to repair or enhance the eye, includes a parallel laser ray tracing (PLRT) system 110. PLRT includes a processor 111 adapted to control the configuration of the probing light bundles and calculate wavefront aberrations based on the sensed location of the reflected light patterns. In this application, patient 114 is positioned on table 112 and the patient's eye is aligned with terminal optics 116. Terminal optics 116 are mounted on arm 118 which extends from post 120. Preferably, arm 118 and post 120 are adjustable to permit easy alignment. Preferably, terminal optics 116 includes the optical components of the PLRT system and is interconnected with processor 111. Further, while not always possible, it is desirable that terminal optics 116 also include the surgical treatment device, such as a laser, to perform the necessary procedure on the patient without realignment. Images generated by the PLRT system or other cameras may be displayed on display 124. The alignment of the system may be adjusted by joystick 122. Still more preferably, the joystick may control the PLRT system to recalculate the wavefront aberrations after each movement of the system.

Figure 9:
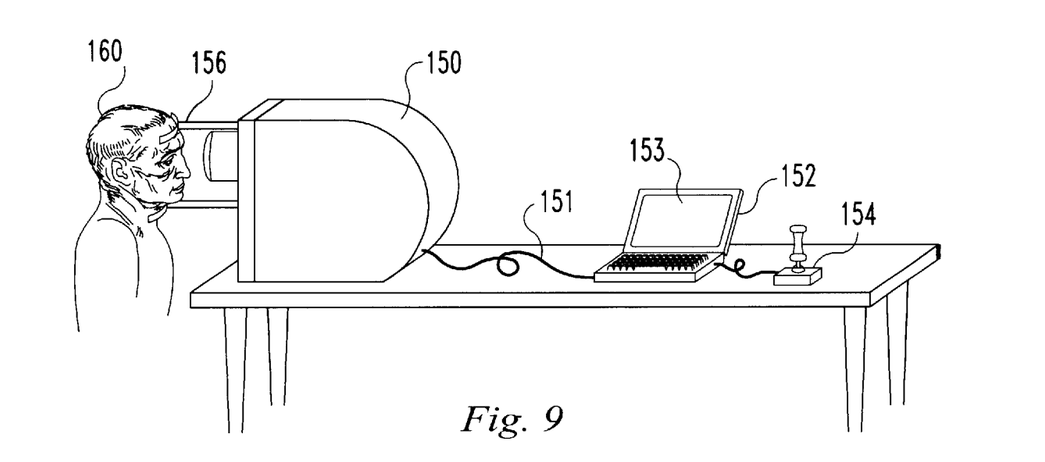
FIG. 9 is a diagrammatic view of a second system incorporating the present invention.

In still a further application of the present invention shown in FIG. 9, the PLRT system 150 is used in conjunction with a fundus imaging system. The patient 160 is positioned in a chin rest 156 and aligned with the PLRT system. The PLRT system is connected to computer 152 by cable 151 such that data concerning alignment, zoom, etc. may be sent to the PLRT system and the PLRT system may return the desired sensor results. In one form of the invention, a joystick 154 may be utilized to guide the PLRT system and other elements of the fundus imaging system to the desired points of interest. It will be appreciated that the resolution of the PLRT system may initially be set low for relatively wide views of the eye to permit the operator to locate structures of interest and that the resolution of the PLRT system may be increased by the operator to obtain more detailed images of the various structures of the eye. The operator may seek greater resolution or may increase magnification with the need for greater resolution. In this manner, the operator may navigate the fundus imaging system to obtain any number of images of the interior portions of the eye. It will be understood that computer 152 may display the most recent image on monitor 153 and may write data to a file for each acquired image. Each of the acquired images may be indexed to the appropriate region of the eye such that all of the acquired images may be digitally linked to form a complete image of the interior elements of the eye. In this manner, the patient's images may be stored for later analysis by a skilled reader or for comparison to future images of the patient that may indicate degeneration or healing in the interior of the eye.

In a preferred method of utilizing the above described system, a human eye is evaluated. In this use, the system is calibrated as previously described. With the aid of an alignment camera (not shown), align the patient's eye so that a central ray is incident on or near the fovea of the retina. Once the patient's eye has been generally brought into the optical path of the sensing system, the system may perform the alignment sequence described above to compensate for any remaining misalignment.

The system is then controlled to turn on pre-determined, first pattern of rays via the SLM. Preferably, the first pattern of rays includes a plurality of substantially parallel light rays. An image of the first pattern of rays is captured by the reference camera and a corresponding image of the first reflected (from the eye) pattern is captured by the sample camera. A computer or other processor utilizes the information about the first pattern and the first reflected pattern to calculate the wavefront given by the sample. The SLM is then controlled to produce a second pattern of rays. In most instances, this second pattern will include a plurality of rays, shifted slightly from the first pattern. Again the second pattern is captured by the reference camera and a second reflected pattern is captured by the sample camera. The computer will again use the sensed information to calculate a wavefront. The process of controlling the SLM to change the pattern of incident rays continues until sufficient information is gathered to accurately re-construct the wavefront of the eye.

Information about the wavefront of the eye may be used for a wide variety of applications. In a first instance, digital images of the interior of the eye may be obtained by passing visible light into the eye and reconstructing the sensed image via pixel manipulation according to the wavefront aberrations to generate a distortion-limited image. This image may be used for diagnostics or for direct surgery. Further, the system may calculate modifications necessary to the optics of the human eye such that a laser or other instrument removes a portion of the human eye to improve patient vision. Still further, corrective optics substantially matching or compensating for the calculated aberrations may be generated to improve patient vision. Such corrective optics may include, for example but without limitation, programmable adaptive optic devices and lenses.

Calculations

In the current invention, a digital image is reconstructed on a pixel-by-pixel basis by applying transform information stored in a pixel map. Although each pixel can be transformed in a number of ways, the pixel displacement transform is of primary importance. It is contemplated that at least three different techniques may be utilized for generating the displacement information in the pixel map (the information necessary to relocate pixels during the reconstruction process). These techniques include Wavefront Modeling, Direct Displacement Mapping and Inverted Mapping.

The wavefront can be thought of as the surface of a light wave emanating from a point on the retina, and is a fundamental description of the overall quality of the optical system. The aberration wavefront is defined as the difference between the real wavefront and a reference wavefront. It is typical to use for a reference surface, a spherical wavefront that emanates from a point on the pupil.

In the method described below, laser displacements are first curve fitted to a set of equations representing the aberration wavefront of the eye. The aberration wavefront equation provides a continuous mathematical solution to calculate translation values for each pixel in the acquired image. The first part of this method, curve fitting displacement data to aberration wavefront equations, has been described by Navarro and Losada. It is noted that the calculations are similar to those used with data acquired from a HS device.

The wavefront equation is typically represented by a special set of polynomials, called Zernike polynomials, although it is possible to use other polynomial forms. The aberration wavefront equation, W(x, y), is written in terms of Zernike polynomials as:

$$W(x, y) = \sum_{i=1}^{M} C_i Z_i(x, y) \tag{0.1}$$

where $C_i$ are coefficients of the Zernike polynomials, $Z_i(x, y)$. The Zernike polynomials are especially relevant to ophthalmic applications since many aspects of vision, like defocus, astigmatism, spherical aberrations, and higher-order aberrations can be quantified by specific Zernike coefficients (see Table 1).

To calculate the aberration wavefront of the eye, we first make use of the fact that displacements of individual rays from their ideal locations can be equated to the slope of the wavefront at the location of the ray in the pupil plane:

$$\Delta X(x, y) = \frac{\partial W(x, y)}{\partial x} \tag{0.2}$$

$$\Delta Y(x, y) = \frac{\partial W(x, y)}{\partial y}$$

Combining equations (0.1) and (0.2) yields:

$$\frac{\partial W(x, y)}{\partial x} = \sum_{i=1}^{M} C_i \frac{\partial Z_i(x, y)}{\partial x} \tag{0.3}$$

$$\frac{\partial W(x, y)}{\partial y} = \sum_{i=1}^{M} C_i \frac{\partial Z_i(x, y)}{\partial y}$$

To obtain the Zernike coefficients, $C_i$, equation (0.3) is written as a linear system, which can be solved using the method of least squares. Following the technique of modal estimation outlined by Southwell, we can write the matrix equation:

$$S = CA \tag{0.4}$$

where S is a vector containing displacement (slope) measurements, C is a vector containing unknown Zernike coefficients, and A is a rectangular matrix with M columns (corresponding to the number of Zernike terms) and $2N^2$ rows ($2N^2$ is the number of displacement data points). It is noted that the normal equations are not ill conditioned so the standard least-squares solution can be used to obtain the Zernike coefficients:

$$A^t A C = A^t S \tag{0.5}$$

and $$C = (A^t A)^{-1} A^t S \tag{0.6}$$

In equation (0.6), the transformation matrix $A^t A$ is known, and $A^t S$ is a vector whose components are weighted sums of the displacement data. Table 1 shows Zernike polynomials up to $4^{th}$ order and corresponding relationships to vision-related parameters.

TABLE 1

Zernike Polynomials up to Fourth Degree.

| Term | Zernike Polynomial | Monomial Representation | Meaning |
|---|---|---|---|
| $Z_0(x,y)$ | 1 | 1 | Piston or constant term |
| $Z_1(x,y)$ | $\rho\sin\theta$ | x | Tilt in x direction |
| $Z_2(x,y)$ | $\rho\cos\theta$ | y | Tilt in y direction |
| $Z_3(x,y)$ | $\rho^2\sin(2\theta)$ | $2xy$ | Astigmatism with axis at ±45° |
| $Z_4(x,y)$ | $2\rho^2 - 1$ | $-1 + 2y^2 + 2x^2$ | Focus shift |
| $Z_5(x,y)$ | $\rho^2\cos(2\theta)$ | $y^2 - x^2$ | Astigmatism with axis at 0° or 90° |
| $Z_6(x,y)$ | $\rho^3\sin(3\theta)$ | $3xy^2 - x^3$ | Triangular astigmatism with base on x axis |
| $Z_7(x,y)$ | $(3\rho^3 - 2\rho)\sin\theta$ | $-2x + 3xy^2 + 3x^3$ | Third-order coma along x axis |
| $Z_8(x,y)$ | $(3\rho^3 - 2\rho)\cos\theta$ | $-2y + 3y^3 + 3x^2y$ | Third-order coma along y axis |
| $Z_9(x,y)$ | $\rho^3\cos(3\theta)$ | $y^3 - 3x^2y$ | Triangular astigmatism with base on y axis |
| $Z_{10}(x,y)$ | $\rho^4\sin(4\theta)$ | $4y^3x - 4x^3y$ | |
| $Z_{11}(x,y)$ | $(4\rho^4 - 3\rho^2)\sin(2\theta)$ | $-6xy + 8y^3x + 8x^3y$ | |
| $Z_{12}(x,y)$ | $6\rho^4 - 6\rho^2 + 1$ | $1 - 6y^2 - 6x^2 + 6y^4 + 12x^2y^2 + 6x^4$ | Third-order spherical aberration |
| $Z_{13}(x,y)$ | $(4\rho^4 - 3\rho^2)\cos(2\theta)$ | $-3y^2 + 3x^2 + 4y^4 - 4x^2y^2 - 4x^4$ | |
| $Z_{14}(x,y)$ | $\rho^4\cos(4\theta)$ | $-y^4 - 6x^2y^2 + x^4$ | |

Once the measured (aberrated) wavefront has been modeled, the equation provides a continuous function with which displacement values can be calculated. Returning to Equation (0.2), the variables $\Delta X$ and $\Delta Y$ correspond to the distance a ray is displaced that has passed through the point (x, y), in the pupil plane. However, in an acquired image, the pixels have already been displaced and the inverse of the displacement is the information of interest. This inverted value represents the ideal location for the ray and is stored in the pixel map. Data points would preferably be calculated at intervals determined to match pixel center distances. This would provide translation information for each pixel in the image. Errors due to misalignment would be minimized.

The steps for reconstructing an image using the method of wavefront modeling may be as follows:

1. Capture spot locations for bundles of laser beamlets reflected from the cornea.
2. Acquire a digital image of the region of interest.
3. Subtract background noise and any aberration due to system optics
4. Calculate the aberration wavefront equation as described in the previous section.
5. For each pixel in the region of interest, calculate the amount of displacement that has occurred from the aberration wavefront equation.
6. Take the inverse as the translation that needs to occur to move the pixel to its ideal location.
7. For pixels that overlap, perform an average, weighted average or apply some other smoothing algorithm to determine the final pixel value.
8. For holes in the image, use the technique of image infilling (described in more detail below), interpolation, or some other appropriate algorithm to supply missing data.
9. Repeat steps as necessary to obtain a clear image.

A further technique utilizes an index of the incident rays. The problem of indexing rays is not a trivial one, and becomes increasingly difficult as the number of spots recorded by the sensor increases. Overlapping beamlets would introduce errors in displacement calculations. Fortunately, the programmable nature of the SLM allows flexibility in pattern generation. For discussion, it is convenient to define a beamlet interval, I, that is the distance between beams that are turned "On" by the SLM. If the minimum interval needed to guarantee no spot overlap at the sensor, $I_{min}$, is known then it is possible to guarantee no spot overlap will occur. This is accomplished by applying in a sequential fashion, several patterns with beamlets spaced at least $I_{min}$ apart. Although this reduces the number of data points that can be recorded simultaneously (in a parallel fashion) the overall number of data points is still tremendous.

As an example, if the minimum beamlet spacing necessary to require no spot overlap was 153 microns. Then every $10^{th}$ micromirror in a DMD would be turned on—nine micromirrors would be turned off between each micromirror that was turned on. The system could turn on the first pattern of beamlets, capture the spot information, then shift the beamlet pattern 17 microns (one micromirror) to one side. The system could then acquire spot information for the remaining frames, each shifted by one micromirror so that the sensor recorded all beamlet locations. Since the DMD can change mirror states at rates up to one kHz, all frames could be recorded in less time than is required for the eye to move. All frames would need to be recorded within time limitations governed by saccade movements of the eye.

Nearest neighbor spacing provides an alternative to individual beamlet indexing. With nearest neighbor spacing, it may be possible to simply measure the distance between neighboring beamlets to obtain localized average beamlet displacements. Since, in an ideal optical system, each beamlet travels along a path parallel to its neighbor, it would be possible to predict theoretical beamlet spacing. The reference camera provides information about aberrations in the system that can be subtracted from sample calculations. So differences between neighboring spot locations could be used to calculate displacement and, if patterns consisting of beamlets spaced $I_{min}$ were employed, then no indexing would be required. Calculations would simply be based on nearest neighbor spacing.

It may be possible to identify in a laboratory a threshold value for $I_{min}$ that works for a majority of patients. However, given the tremendous variability in the human optical system, this is unlikely. It is more likely that the system would need to gather some preliminary information that is patient dependent, like a suitable value for $I_{min}$. This would likely occur as part of a patient alignment and calibration sequence just prior to making measurements. Again, the speed of the system would be relied upon to capture information in short time intervals.

The pattern of beamlets would first contain a large value for $I_{min}$, so that only a few beamlets were turned on. The sensor would record spot locations and determine whether the interval value could be reduced. If yes, then more beamlets would be turned on and the corresponding spot locations recorded by the sensor. This process would be repeated until the system determined that the smallest acceptable value for $I_{min}$ was reached. The smallest value for $I_{min}$ will be influenced by regions having large aberrations, and system-related parameters like magnification (which will impact the number of sensor pixels allocated to measure displacement of each beamlet). Techniques like indexing or nearest neighbor spacing would be used to determine $I_{min}$ during the calibration procedure. The use of an eye-tracking camera would be beneficial for measuring saccade movement in the eye.

Direct Displacement Mapping

Returning to equation (0.2) we note that the displacement of each spot corresponds to the slope of the aberration wavefront at the location of the beamlet. That is, the displacement is the distance a beamlet has been displaced due to the media in front of the eye. In the technique described previously, the data was fitted to a model that described the aberration wavefront of the eye. The wavefront equation provided a continuous function that could be used to retrieve displacement information anywhere within the region of interest. This data-fitting technique is necessary when the grid of data points is relatively sparse compared to the pixel resolution in the image.

If, however, the resolution of the grid of data points approaches the resolution for the region of interest, then the spot displacement for each beamlet can be used directly to provide pixel translation information. The computational overhead is greatly reduced, and the technique eliminates mathematical errors from fitting routines. The drawback to this approach lies in the fact that translation information is known only for those pixels in the acquired image that are located where laser spots have been recorded. Some pixels will have no translation information in the pixel map. However, it is theoretically possible for the number of spots to approach the pixel resolution in the acquired image.

Once the acquired image has been reconstructed so that pixels with known translation information have been moved to their ideal positions, missing pixels can be estimate using interpolation, or other algorithm. In an article entitled "Image Inpainting" reprinted from the Institute for Mathematics and its Applications, University of Minnesota (1999), Bertalmio and co-workers have recently introduced an algorithm that automatically fills in regions of missing data in a digital image. The technique, called "Image Inpainting," considers surrounding gray levels and vector fields so that both color and structure are interpolated.

Inverted Mapping

The third technique offered here demonstrates the flexibility of the programmable SLM and may offer increased accuracy over the previous two techniques. The principle is derived from the observation that Zernike polynomials are orthogonal only when the number of data points are large and they are uniformly distributed over the pupil plane. Typically, these limiting conditions are overcome by first using Gram-Schmidt orthogonalization to fit the data to other orthogonal polynomials that are then transformed into Zernike polynomials. However, this process can be computationally intensive.

In this technique, information from the source as well as the target is used to create the translation pixel map. Individual beamlets are selectively turned on until the pattern of spots recorded by the sample sensor has an even or uniform distribution. When there is even spacing between spots on the sample sensor, then the source image represents a map of the distortion required to make a clear image as seen by the sample sensor through the distorted media. The source image can be used to provide information necessary to reconstruct an image so that the distortion is removed. In general terms, those neighboring beamlets that have spots recorded with spacing farther apart than the average interval would correspond to pixels in the acquired image that need to be translated closer together. Similarly, neighboring beamlets with recorded spot interval less than the average would correspond to pixels that should be translated away from each other in the reconstructed image.

Mirror Approximation

In still a further preferred technique, a mirror may be adjusted to shape an illumination beam prior to transmission into the eye to approximate the aberrations of the eye. In this application, a programmable DMD device is initially configured to transmit a first configuration of parallel sensing beams generated by an energy source. The location of the sensing beams in the first configuration is recorded by a reference sensor and the location of beams after reflection from the eye (the first reflected configuration) is recorded by the primary sensor. The DMD device may then be controlled to reflect a beam from the energy source to reproduce the first reflected configuration on the reference sensor. In this manner, the DMD is being controlled to correct the incident wavefront for the approximate aberrations in the optics of the eye. An illumination source may then transmit light onto the DMD for transmission into the eye and the reflected image may be recorded by the primary sensor. The process of controlling the DMD to compensate for the sensed aberrations for each configuration of the sensing beams may be continued until the entire area of interest is imaged. In this manner, the entire corrected image may be constructed.

Alternatively, a plurality of sensing beam configurations may be transmitted and recorded sequentially both by the reference sensor and by the primary sensor. The DMD device may then be programmed to best approximate the wavefront aberrations and an illumination source may then be reflected off the DMD to illuminate structures in the eye. In this manner, it is contemplated that a substantially complete image may be acquired with a single use of the illumination source.

In the PLRT device of the present invention, laser points emanate from the source along a collimated path. There is no additional angle of incidence induced from scanning mirrors as in the LRT technique (which results in artificial astigmatism). The flexibility of the system offers many applications. For example, one could "Turn On" bundles of rays in the shape of a circle to simulate a large beam (like that used in the HS device). Compared to the HS device, no lenslet array is needed since beamlets in the large bundle are selectively "turned on" providing point-by-point information about the wavefront of the larger beam. In essence, the PLRT technique allows you to measure displacement throughout the larger beam, by blocking information from neighboring beamlets by turning off those neighboring beamlets at the source.

Analysis of individual spot displacement is nearly identical to that of the HS device. Each beamlet, passing through the eye and reflecting from the retina, will emerge from the eye with a distorted wavefront. In Navarro's device, all beamlets come from the same point and the trajectories are controlled by moving or scanning mirror(s). The beamlet, imaged by the sensor will have a centroid position that is displaced from the ideal. This displacement is proportional to the aberration structure of the eye along the path of the beamlet as it passes through the eye in its first pass. It is possible to use a similar technique in the present device to determine the location of the central ray. Individual spot locations are then referenced from this location.

The ideal location of each beamlet can be determined in a number of ways. First, the pixel location within the array of micromirrors is known. It is possible to place a second "Reference" sensor opposite the beam splitter so that a portion of the light passes through to the reference sensor. The location of each beamlet in the reference sensor would be used as the ideal position for that particular beamlet. The important advantage of this method is that aberrations in the optics of the device could be eliminated from calculations.

Other laser-scanning methods use beams that are very large compared to surface features of the retina. One beamlet may cover several features. Portions of the beam are reflected at different angles so areal images are distorted, making centroid calculation difficult. The current invention will not suffer as much from these limitations since the incident light reflects from a smaller surface area (with less deviation). The use of smaller beams makes it easier to find the centroid of each beam. Since smaller beams are used, more data points are collected and the data points are more evenly distributed across the wavefront. This helps to ensure that the orthogonality condition of the Zernike polynomials is met, increasing the accuracy of the calculations.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for imaging through an optical system with an aberration, comprising:

an energy source co-operable with a spatial light modulator adapted to generate a plurality of electromagnetic beams having a first configuration for simultaneous transmission through the optical system;

a sensor for detecting said plurality of electromagnetic beams after passing through the optical system, said sensor producing at least one signal in response to said plurality of electromagnetic beams; and a processor adapted to utilize said at least one signal to approximate the aberrations in the optical system.

2. The system of claim 1, wherein said spatial light modulator is programmable to produce a second configuration different than said first configuration.

3. The system of claim 2, wherein said spatial light modulator includes at least 100 elements which may be controlled to generate a corresponding number of individual electromagnetic beams.

4. The system of claim 3, wherein said spatial light modulator includes at least 1,000 elements which may be controlled to generate a corresponding number of individual electromagnetic beams.

5. The system of claim 4, wherein said spatial light modulator includes at least 10,000 elements which may be controlled to generate a corresponding number of individual electromagnetic beams.

6. The system of claim 5, wherein said spatial light modulator includes at least 100,000 elements which may be controlled to generate a corresponding number of individual electromagnetic beams.

7. The system of claim 4, wherein said spatial light modulator is controllable to produce a plurality of electromagnetic beam configurations for transmission though the optical system of the eye.

8. The system of claim 1, wherein said spatial light modulator is controllably reflective.

9. The system of claim 1, wherein said spatial light modulator is controllably transmissive.

10. The system of claim 1, wherein said first configuration is sized to correspond to the diameter of the pupil of a human eye.

11. The system of claim 1, wherein said plurality of electromagnetic beams are spaced apart from each other by at least 0.25 micron.

12. The system of claim 1, wherein said sensor is an array with a maximum sensitivity to distinguish neighboring beams and said plurality of electromagnetic beams are spaced apart from each other by a minimum interval corresponding to said maximum sensitivity.

13. The system of claim 1, wherein said energy source comprises a plurality of laser emitting diodes.

14. The system of claim 1, wherein said energy source includes a laser.

15. The system of claim 1, further including a reference sensor adapted to sense said first configuration before transmission through the optical system and to produce a corresponding reference signal, said processor utilizing said at least one signal and said reference signal to approximate the aberration in the optical system.

16. A system for correction of optical aberrations of a living eye, comprising:

means for generating a plurality of electromagnetic beams in a first configuration for simultaneous transmission into the living eye;

a sensor for detecting said plurality of electromagnetic beams after reflection from the living eye, said sensor producing an output signal corresponding to the sensed electromagnetic beams; and a processor connected to receive said output signal, said processor adapted to utilize said output signal to approximate aberrations of the living eye, wherein said plurality of electromagnetic beams are spaced apart from each other by at least 0.25 microns.

17. The system of claim 16, further including a reference sensor adapted to sense said first configuration before transmission through the optical system and to produce a corresponding reference signal, said processor utilizing said output signal and said reference signal to approximate aberrations in the living eye.

18. The system of claim 16, wherein said sensor is an array with a maximum sensitivity to distinguish neighboring beams and said plurality of electromagnetic beams are spaced apart from each other by a minimum interval corresponding to said maximum sensitivity.

19. The system of claim 16, wherein said means for generating a plurality of electromagnetic beams is controllable to produce a plurality of electromagnetic beam configurations for transmission through the optical system of the eye.

20. Apparatus for use in performing surgery on a living eye, said apparatus comprising:

a spatial light modulator generating a plurality of electromagnetic beams for simultaneous transmission into a living eye;

a camera located adjacent the eye and in the optical path of a substantial number of said plurality of electromagnetic beams reflected from the living eye, said camera adapted to produce digital outputs corresponding the sensed location of said substantial number of said plurality of electromagnetic beams;

a processor connected to receive said outputs from said camera and for converting said output signals to a digital signal representative of the optics of the living eye; and surgical equipment connected to receive said digital signal representative of the optics of the living eye and for performing surgery on the living eye.

21. The apparatus of claim 20, wherein said surgical equipment includes a display device for displaying images of the eye.

22. The apparatus of claim 20, wherein said surgical equipment includes a laser for shaping optical components of the eye.

23. Apparatus for generating corrective optic devices adapted to correct for wave aberrations of the living eye, comprising:

a spatial light modulator generating a plurality of electromagnetic beams in a first configuration for simultaneous transmission into the living eye;

means for receiving a reflected image of said electromagnetic beams from the living eye and generating an output signal in response to the received reflected image; and a processor for calculating wave aberrations of the living eye based on the difference between said first configuration incident upon the living eye and said reflected image; said processor providing output data for generating a corrective optics device substantially correcting the calculated wave aberrations.

24. The apparatus of claim 23, further including at least one lens fabrication system connected to said processor, said lens fabrication system creating a lens substantially correcting the calculated wave aberrations.

25. The apparatus of claim 23, further including an adaptive optic device controllable by said processor to correct for the calculated aberrations.

26. Apparatus for use in performing surgery on the living eye, said apparatus comprising:

a spatial light modulator generating a plurality of electromagnetic beams in a first configuration for simultaneous transmission into the living eye;

means for receiving a reflected image of said electromagnetic beams from the living eye and generating an output signal in response to the received reflected image; and a processor for calculating wave aberrations of the living eye based on the difference between said first configuration incident upon the living eye and said reflected image; and means for performing surgery on the living eye in response to the calculated wave aberrations from said processor.

27. The apparatus of claim 26, wherein said means for performing surgery includes a laser.

28. The apparatus of claim 26, wherein said means for receiving includes an array of charge coupled devices.

29. Apparatus for generating high resolution fundus images of the living eye, said apparatus comprising:

an energy source adapted to generate a plurality of electromagnetic beams in a first configuration for simultaneous transmission into the living eye;

a reference sensor adapted to sense said first configuration before transmission through the optical system and to produce a corresponding reference signal;

a sensor adapted to receive a reflected image of a substantial number of said electromagnetic beams from the living eye and generating an output signal in response to the received reflected image;

a processor operable to determine aberrations of the living eye based on the difference between said first configuration transmitted into the living eye and said reflected image said processor utilizing said output signal and said reference signal to approximate the aberrations in the optical system;

a camera for receiving a fundus image of the living eye; and a display device receiving an output from said processor corresponding to said fundus image corrected based on the calculated aberrations.

30. The apparatus of claim 29, wherein said energy source is controlled by said processor to generate a plurality of configurations to transmit electromagnetic beams through different portions of the living eye.

31. The apparatus of claim 29, wherein said processor comprises at least a first processing unit for calculating wave aberrations of the living eye and a second processing unit for providing said output corresponding to said image of the retina corrected based on the calculated wave aberration.

32. A method for detecting aberrations of the living eye, comprising:

generating a plurality of electromagnetic beams in a first configuration;

providing a reference sensor and sensing said first configuration;

transmitting said first configuration of electromagnetic beams into a living eye;

receiving a reflected image of said first configuration and generating digital signals corresponding to said reflected image; and calculating wave aberrations of the eye, using said digital signals.

33. The method of claim 32, further including receiving the calculated wave aberrations for performing laser surgery of said living eye.

34. The method of claim 32, further including receiving a fundus image of a living eye and correcting the fundus image on the basis of the calculated wave aberrations.

* * * * *